United States Patent [19]

Maye et al.

[11] Patent Number: 6,113,920
[45] Date of Patent: Sep. 5, 2000

[54] PHARMACEUTICAL COMPOSITIONS

[75] Inventors: Katherine Jeannette Maye, Durham; Gary Wayne Goodson, Raleigh; Allen Wayne Wood, Cary, all of N.C.

[73] Assignee: Glaxo Wellcome Inc., Research Triangle Park, N.C.

[21] Appl. No.: 08/955,635

[22] Filed: Oct. 23, 1997

Related U.S. Application Data

[60] Provisional application No. 60/029,240, Oct. 31, 1996.

[30] Foreign Application Priority Data

Oct. 31, 1996 [GB] United Kingdom ................... 9622681

[51] Int. Cl.$^7$ ....................................................... A61F 13/00
[52] U.S. Cl. .......................... 424/400; 424/422; 424/434; 424/435; 514/262; 514/274
[58] Field of Search ..................................... 424/400, 422, 424/434, 435; 514/262, 274

[56] References Cited

U.S. PATENT DOCUMENTS

| | | |
|---|---|---|
| 5,047,407 | 9/1991 | Belleau et al. . |
| 5,204,466 | 4/1993 | Liotta et al. . |
| 5,532,246 | 7/1996 | Belleau et al. . |
| 5,539,116 | 7/1996 | Liotta et al. . |
| 5,859,021 | 1/1999 | Cameron et al. ........................ 514/274 |

FOREIGN PATENT DOCUMENTS

| | | |
|---|---|---|
| 0 513 917 A1 | 11/1992 | European Pat. Off. . |
| 0 513 917 | 12/1995 | European Pat. Off. . |
| 7-109221 | 4/1995 | Japan . |
| 91/17159 | 11/1991 | WIPO . |
| 92/20344 | 11/1992 | WIPO . |
| 95/29174 | 11/1995 | WIPO . |
| 95/33464 | 12/1995 | WIPO . |
| 96/26734 | 9/1996 | WIPO . |
| 96/30025 | 10/1996 | WIPO . |
| 97/33565 | 9/1997 | WIPO . |

OTHER PUBLICATIONS

Ford, Katherine, et. al, "Investigations Leading To The Elimination of Segregation in a Direct Compression Combination Product," *Pharmaceutical Research*, Sep. 1996 (Supplement), vol. 13, No. 9, p. S206 (PT 6198).

Hammer, Scott M., "Advances in antiretroviral therapy and viral load monitoring," *One world. One hope, XI International Conference on AIDS*, 1996 vol. 10 (suppl 3):S1–S11.

St. Clair, M.H., et. al., "In vitro antiviral activity of 141W94 (VX–478) in combination with other antiretroviral agents," *Antiviral Research* 29 (1996) 53–56.

Tisdale, Margaret, et. al., "Rapid in vitro selection of human immunodeficiency virus type 1 resistant to 3'—thiacytidine inhibitors due to a mutation in the YMDD region of reverse transcriptase," *Proc. Natl. Acad. Sci. USA*, vol. 90, pp. 5653–5656. Jun. 1993 Medical Sciences.

Glaxo Wellcome Retrovir® (zidovudine) Tablets, Capsules and Syrup Product Information Package Insert, Glaxo Wellcome Inc., Research Triangle Park, NC 27709, Sep. 1996.

Glaxo Wellcome Epivir® Tablets Solution (lamivudine tablets) and Epivir® Oral (lamivudine oral solution) Product Information Package Insert, Glaxo Wellcome Inc., Research Triangle Park, NC 27709 Aug. 1996.

Rudnic, et. al., "Oral Solid Dosage Forms," *Remington: The Science and Practice of Pharmacy*, vol. II, Chapter 92, pp. 1615–1649.

Editor: Walter Lund, "Oral Solids,"*The Pharmaceutical Codex*, Twelfth Edition, Principles and Practice of Pharmaceutics, 1994, pp. 2–30, The Pharmaceutical Press, London, 1994.

Glaxo Group Limited et al., PCT International Preliminary Examination Report for PCT/EP97/05953, completed Jan. 25, 1999.

*Primary Examiner*—S. Mark Clardy
*Assistant Examiner*—Kathryne E. Shelborne
*Attorney, Agent, or Firm*—Charles E. Dadswell; Karen L. Prus; Jennifer L. Skord

[57] ABSTRACT

A pharmaceutical composition and a method of inhibiting human immunodeficiency virus (HIV) is disclosed which comprises administering to an HIV infected patient a homogenous combination of lamivudine, zidovudine and a pharmaceutical glidant in an amount which achieves antiviral efficacy.

19 Claims, No Drawings

PHARMACEUTICAL COMPOSITIONS

This application claims benefit of provisional application 60/029,240 filed Oct. 31, 1996.

FIELD OF THE INVENTION

The present Invention relates to novel pharmaceutical compositions combining the agents lamivudine and zidovudine into a single dosage form, useful in the treatment of diseases in mammals, including humans.

BACKGROUND OF THE INVENTION

The present Invention relates to novel pharmaceutical compositions combining the agents lamivudine and zidovudine into a single dosage form, useful in the treatment of diseases in mammals, including humans. The present Invention is particularly useful for treating viral infections, particularly retroviral infections, including human immunodeficiency virus (HIV).

HIV causes a variety of clinical conditions including acquired immune deficiency syndrome (AIDS) and chronic neurological disorders. The recent advent of a variety of multiple-drug treatment regimens has dramatically improved the treatment of HIV infected patients. Prior to these multiple-drug regimens, treatment was often limited to single drugs with limited effectiveness.

Single drug treatment regimens typically require long term treatment increasing the incidence of unwanted side effects. Moreover, single drug therapies are particularly vulnerable to mutations in the HIV virus, leading to drug resistant variants of HIV.

The use of multiple drug therapies may reduce the development of drug-resistant strains of HIV because one drug will usually cancel out mutations against other drugs. Multiple-drug therapies may even inhibit replication of HIV viruses for a period of time sufficient to eliminate HIV from the body.

The success of modern multiple-drug treatments for HIV often requires strict compliance with a complex treatment regimen that can require the administration of many different drugs per day, administered at precisely timed intervals with careful attention to diet. Patient non-compliance is a well known problem accompanying such complex treatment regimens. See Goodman & Gilman, The Pharmacological Basis of Therapeutics, 9th ed., pp. 1704–1705 (1996), incorporated herein by reference. Patient non-compliance is an important problem in the treatment of HIV because such noncompliance may lead to the emergence of multiple-drug resistant strains of HIV.

Two of the many compounds which are commonly included in multiple-drug treatment regimens for HIV are zidovudine and lamivudine. Lamivudine (also known as 3TC[TM1]) is a synthetic nucleoside analogue, chemically known as (2R,cis)-4-amino-1-(2-hydroxymethyl-1,3-oxathiolan-5-yl)-(1H)-pyrimidin-2-one. Lamivudine has also been referred to as (−)2',3'-dideoxy, 3'thyacytidine. Lamivudine has proven antiviral activity against human immunodeficiency virus (HIV) and other viruses such as hepatitis B. Lamivudine is commercially available from Glaxo Wellcome Inc. under the tradename EPIVIR[TM2].

[1] 3TC is a trademark of the Glaxo Wellcome group of companies. Registered in the United States Patent and Trademark office.
[2] EPIVIR is a trademark of the Glaxo Wellcome group of companies. Registered in the United States Patent and Trademark office.

Zidovudine, chemically known as 3'-azido-3'-deoxythymidine, is a pyrimidine nucleoside analogue commercially available from Glaxo Wellcome Inc. under the tradename RETROVIR[TM3] for the treatment of HIV and other viruses. Zidovudine is further described in U.S. Pat. Nos. 4,818,538, 4,828,838, 4,724,232, 4,833,130 and 4,837,208, all of which are incorporated herein by reference.

[3] RETROVIR is a trademark of the Glaxo Wellcome group of companies. Registered in the United States Patent and Trademark office.

In November of 1995, the FDA granted accelerated approval for the use of lamivudine in combination with zidovudine for first-line treatment of HIV-infection in adults and children. It is now known that lamivudine exhibits unexpected advantages when used in combination with known inhibitors of HIV replication. In particular, lamivudine shows a synergistic antiviral effect and/or reduction in cytotoxicity when used in combination with zidovudine. In controlled clinical trials, combination therapy with lamivudine and zidovudine delayed the emergence of zidovudine-resistant mutations of HIV.

Segregation of active ingredients in pharmaceutical powders and granulations is a widely recognized problem that can result in inconsistent dispersions of the active ingredients in final dosage forms. Some of the main factors contributing to segregation are particle size, shape and density. Segregation is particularly troublesome when attempting to formulate a single homogenous tablet containing multiple active ingredients having different densities and different particle sizes. Previous attempts to formulate tablets containing lamivudine and zidovudine were hindered by precisely such segregation problems. Although mixed blends were initially homogeneous, the active ingredients segregated during material handling and prior to tablet compression.

Glidants are substances that have traditionally been used to improve the flow characteristics of granulations and powders by reducing interparticulate friction. See Lieberman, Lachman, & Schwartz, Pharmaceutical Dosage Forms: Tablets, Volume 1, p. 177–178 (1989), incorporated herein by reference. Glidants are typically added to pharmaceutical compositions immediately prior to tablet compression to facilitate the flow of granular material into the die cavities of tablet presses. Glidants include: colloidal silicon dioxide, asbestos free talc, sodium aluminosilicate, calcium silicate, powdered cellulose, microcrystalline cellulose, corn starch, sodium benzoate, calcium carbonate, magnesium carbonate, metallic stearates, calcium stearate, magnesium stearate, zinc stearate, stearowet C, starch, starch 1500, magnesium lauryl sulfate, and magnesium oxide.

Research into the problem of segregation in pharmaceutical compositions has surprisingly demonstrated that glidants can be used to increase and aid blend composition homogeneity. The novel compositions of the present Invention use glidants to effect and maintain homogeneity of active ingredients during handling prior to tablet compression.

It is therefore an object of the present Invention to provide a pharmaceutical formulation combining the active ingredients lamivudine and zidovudine, or pharmaceutically acceptable derivatives thereof, in a sufficiently homogenized form, and a method for using this pharmaceutical formulation.

A further object of the present Invention is to utilize glidants to reduce the segregation of active ingredients in pharmaceutical compositions during pre-compression material handling.

A still further object of the present Invention is to provide a pharmaceutical formulation combining the active ingredients lamivudine and zidovudine, or pharmaceutically acceptable derivatives thereof, with a pharmaceutically acceptable glidant, resulting in a mixture characterized by a pharmaceutically acceptable measure of homogeneity.

Another object of the present Invention is to provide a pharmaceutical formulation comprising zidovudine, or a pharmaceutically acceptable derivative thereof, and lamivudine, or a pharmaceutically acceptable derivative thereof, together with one or more pharmaceutically acceptable carriers and optionally, other therapeutic and/or prophylactic ingredients. The carrier(s) must be pharmaceutically acceptable in the sense of being compatible with the other ingredients of the formulation and not deleterious to the recipient thereof.

Still another object of the present Invention is to simplify treatment regimens for HIV and other viruses with the goal of enhancing patient compliance by providing a simplified dosage form containing pharmaceutically acceptable amounts of lamivudine and zidovudine or pharmaceutically acceptable derivatives thereof. These objects and further objects will become evident from the description of the invention below.

SUMMARY OF THE INVENTION

The present Invention relates to a homogenous pharmaceutical composition, containing two active ingredients of differing particle size, comprising:
 a) a safe and therapeutically effective amount of lamivudine or a pharmaceutically acceptable derivative thereof;
 b) a safe and therapeutically effective amount of zidovudine or a pharmaceutically acceptable derivative thereof; and
 c) a pharmaceutically acceptable glidant.

DETAILED DESCRIPTION OF THE INVENTION

The phrase "safe and therapeutically effective amount," as used herein, means a sufficient amount of a drug, compound, composition, product or pharmaceutical agent to abate or reverse or treat a malady in a human or other mammal without severely harming the tissues of the mammal to which the drug or pharmaceutical agent is administered.

The phrase "pharmaceutically acceptable derivative," as used herein, means any pharmaceutically acceptable salt, solvate, ester, or salt of such ester, or any other compound which, upon administration to the recipient, is capable of providing (directly or indirectly) the intended active ingredient or any active metabolite or residue thereof.

The phrase "safe and effective amount," as used herein is that amount of an agent that is required to perform the function being sought by the researcher or clinician without severely harming the tissues of the mammal to which the agent is administered.

It will be appreciated by those skilled in the art that reference herein to "treatment" extends to both the prophylaxis and the treatment of an established malady, infection or its symptoms.

The compositions of the present Invention employ a safe and therapeutically effective amount of 3'-azido-3'-deoxythymidine (zidovudine) and its pharmaceutically acceptable salts, solvates and derivatives thereof, a safe and therapeutically effective amount (−)2',3'-dideoxy, 3'-thyacytidine (lamivudine) and its pharmaceutically acceptable salts, solvates and derivatives thereof, along with a safe and effective amount of a pharmaceutically acceptable glidant to maintain the compositions homogeneity prior to tablet compression.

The compositions of the present invention may optionally employ a safe and effective amount of a diluent, a safe and effective amount of a disintegrant, and a safe and effective amount of a lubricant or any other safe and effective amounts of excipients commonly used in the art.

Lamivudine

Lamivudine (also known as 3TC™), chemically known as (2R,cis)-4-amino-1-(2-hydroxymethyl-1,3-oxathiolan-5-yl)-(1H)-pyrimidin-2-one and also know as (−)2',3'-dideoxy, 3'thyacytidine, is a synthetic nucleoside analogue with antiviral activity against human immunodeficiency virus (HIV).

In vitro studies have demonstrated that, intracellularly, lamivudine is phosphorilated to its active 5'-triphosphate metabolite (L-TP). The principle mode of action of L-TP is inhibition of reverse transcription via viral DNA chain termination. L-TP also inhibits the RNA- and DNA-dependent DNA polymerase activities of retroviral reverse transcriptase.

Enantiomers of 2',3'-dideoxy, 3'thyacytidine are equipotent against HIV; however, the (−)-enantiomer (lamivudine) has considerably lower cytotoxicity than the (+)-enantiomer. Particularly, the (−)-enantiomer (lamivudine), (−)2',3'-dideoxy, 3'thyacytidine, is provided substantially free of the (+)-enantiomer, that is to say than about 10% w/w of the (+)-enantiomer, particularly no more than about 5%, and more particularly less than about 1% w/w is present. Methods for the preparation of lamivudine are described in WO 92/20669 and WO 95/29174 both incorporated herein by reference.

The phrase "pharmaceutically acceptable derivative of lamivudine" as used herein, means any pharmaceutically acceptable salt, solvate, ester, or salt of such ester, of lamivudine, or any other compound which, upon administration to the recipient, is capable of providing (directly or indirectly) lamivudine or any antivirally active metabolite or residue thereof.

Zidovudine

Zidovudine, chemically known as 3'-azido-3'-deoxythymidine, is a pyrimidine nucleoside analogue. Intracellularly, zidovudine is enzymatically converted to zidovudine triphosphate. Zidovudine triphosphate interferes with the HIV viral RNA dependent DNA polymerase (reverse transcriptase) and thus, inhibits viral replication.

The phrase "pharmaceutically acceptable derivative of zidovudine" as used herein means any pharmaceutically acceptable salt, solvate, ester, or salt of such ester, of zidovudine, or any other compound which, upon administration to the recipient, is capable of providing (directly or indirectly) zidovudine or any antivirally active metabolite or residue thereof. Methods for the preparation of zidovudine are described in U.S. Pat. No. 5,011,829, incorporated herein by reference.

Glidants

Glidants are substances which have traditionally been used to improve the flow characteristics of granulations and powders by reducing interparticulate friction. See, Remington, *The Science & Practice of Pharmacy*, p. 1619, 19th ed. (1995) and see Lieberman, Lachman, & Schwartz, Pharmaceutical Dosage Forms: Tablets, Volume 1, p. 177–178 (1989), both of which are incorporated herein by reference. Improving flow characteristics helps to reduce tablet press clogging and malfunction and minimizes tablet weight variation. Glidants are typically added to pharmaceutical compositions just prior to tablet compression to facilitate the flow of granular material into the die cavities of tablet presses. A commonly used glidant is silicon dioxide ($SiO_2$), also referred to as colloidal silica, fumed silicon dioxide, fumed silica, light anhydrous silicic acid, or silicic anhydride. Silicon dioxide is sold under the tradenames AEROSIL™ and CAB-O-SIL™. Other glidants include asbestos free talc, sodium aluminosilicate, calcium silicate, powdered cellulose, microcrystalline cellulose, corn starch, sodium benzoate, calcium carbonate, magnesium carbonate, metallic stearates, calcium stearate, magnesium stearate, zinc stearate, stearowet C, starch, starch 1500, magnesium lauryl sulfate, or magnesium oxide.

The ability of glidants to improve flow characteristics depends on:

(i) their chemical characteristics in relation to the chemical characteristics of the other ingredients of the composition, and;

(ii) physical characteristics such as the size, shape, and distribution, of the glidants and the other components of the granulation or powder composition, as well as the moisture content and temperature of the composition.

Investigation into the problem of active ingredient segregation in pharmaceutical compositions, powders and granulates has led the present Inventors to the surprising discovery that glidants may be used to reduce segregation of active ingredients and thus improve the homogeneity of pharmaceutical compositions, powders and granulates. The present Invention employs from 0.05% to about 10.0% glidant. Below about 0.05% the homogeneity may not be sufficient and with amounts greater than 10.0% no additional homogeneity is gained.

Silicon dioxide is a preferred glidant because it is relatively inert. A preferred form of silicon dioxide is fumed colloidal silicon dioxide, which is submicroscopic fumed silica. It is a light, non-gritty amorphous powder. Particularly about 0.05% to about 1.0% colloidal silicon dioxide is used because below about 0.05% the homogeneity may not be sufficient and with amounts greater that 1.0% no additional homogeneity is gained.

Where glidants are used to improve flow characteristics, they are typically added to the composition immediately prior to compression during the lubrication step. See, Remington, *The Science & Practice of Pharmacy*, p. 1619, 19th ed. (1995), incorporated herein by reference. However, the present Invention makes use of glidants in the initial mixture to improve and maintain homogeneity during handling prior to compression.

Pharmaceutical Presentation of the Invention

The Invention is preferably presented as a pharmaceutical formulation suitable for oral administration. Such formulations may conveniently be presented as discrete units such as tablets, caplets, or any other form suitable for oral administration and compatible with the compositions of the present Invention, each containing a predetermined amount of the active ingredients. A particularly suitable formulation is a dry compression tablet. Such formulations may contain safe and effective amounts of conventional excipients such as binding agents, fillers, lubricants, or disintegrants. The tablets may also be coated according to any method known to persons skilled in the art that would not interfere with the tablets release properties, or the other physical or chemical characteristics of the present Invention. Tablet coating is further described and delineated by Remington, *The Science & Practice of Pharmacy* 19th ed. 1995 incorporated herein by reference. When desired, the above formulations may also be modified by any method known to persons skilled in the art to achieve sustained release of active ingredients. The formulations may also include a safe and effective amount of other active ingredients, such as antimicrobial agents or preservatives.

These compositions of the present Invention are suitable for administration to humans or other mammals particularly via an oral route of administration. However, other routes as utilized by medical practitioners and others skilled in the art of pharmaceutical dosage administration such as Pharmacists and Nurses are not foreclosed. One such method would be the crushing of a solid dosage form, mixing with a suitable administration vehicle and administering rectally as an enema. Other routes of administration might include: topical and inhalation.

It will be appreciated by those skilled in the art that the amount of active ingredients required for use in treatment will vary according to a variety of factors, including the nature of the condition being treated and the age and condition of the patient, and will ultimately be at the discretion of the attending physician, veterinarian or health care practitioner. In general, however, the current recommended oral dose of lamivudine for adults and adolescents is 150 mg twice daily administered in combination with zidovudine. For adults with low body weights (less than 50 kg or 110 lb.) the current recommended oral dose of lamivudine is 2 mg/kg twice daily administered in combination with zidovudine. The recommended oral dose of lamivudine in pediatric patients 3 months to 12 years of age is 4 mg/kg twice daily, up to a maximum of 150 mg twice daily administered in combination with zidovudine.

In general, the current recommended oral dose of zidovudine is 600 mg per day in divided doses in combination with other antiretroviral agents. The recommended oral dose in pediatric patents 3 months to 12 years of age is 180 mg/m$^2$ every 6 hours or 720 mg/m$^2$ per day not to exceed 200 mg every 6 hours.

Compositions of the present Invention enable patients greater freedom from multiple dosage medication regimens and ease the needed diligence required in remembering complex daily dosing times and schedules. By combining lamivudine and zidovudine in to a single dosage form, the desired daily doses may be presented in a single dose or as divided doses, particularly as divided doses, administered at appropriate intervals, for example as two, three, four or more sub-doses per day, particularly as two sub-doses per day.

The compositions of the present Invention conveniently allow administration of two separate compounds in unit dosage form containing, for example, from about 15 to about 1000 mg of lamivudine, particularly from about 100 to about 500 mg of lamivudine and most particularly 150 mg of lamivudine, and from about 30 to 1000 mg of zidovudine, particularly from about 200 mg to about 500 mg zidovudine and most particularly 300 mg of zidovudine per unit dosage form.

The composition of the present Invention may be used in combination with other pharmaceutical formulations as a component of a multiple drug treatment regimen.

Compositions of the present Invention may also be packaged as articles of manufacture comprising a safe and therapeutically effective amount of lamivudine, or a pharmaceutically acceptable derivative thereof; a safe and therapeutically effective amount of zidovudine, or a pharmaceutically acceptable derivative thereof and a safe and effective amount of a pharmaceutically acceptable glidant.

Any of the various methods known by persons skilled in the art for packaging tablets, caplets, or other solid dosage forms suitable for oral administration, that will not degrade the components of the present Invention, are suitable for use in packaging. Tablets, caplets, or other solid dosage forms suitable for oral administration, may be packaged and contained in various packaging materials particularly glass and plastic bottles and also including unit dose blister packaging. The packaging material may also have labeling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with a pharmaceutical article of manufacture. The package insert and any article of manufacture labeling provides information relating to the pharmaceutical composition. The information and labeling provides various forms of information utilized by health-care professionals and patients, describing the composition, its dosage and various other parameters required by regulatory agencies such as the United States Food and Drug Agencies.

Method of Manufacture

The compositions of the present Invention can be formulated using methods and techniques that are suitable for the compositions' physical and chemical characteristics and that are commonly employed by persons skilled in the art in preparing oral dosage forms utilizing a dry press granulation. Remington, *The Science & Practice of Pharmacy*, p. 1615–1623, 1625–1648, and other applicable sections, 19th ed. (1995).

Composition Use

Compositions of the present Invention in their method aspect are administered to a human or other mammal in a safe and effective amount as described herein. These safe and effective amounts will vary according to the type and size of mammal being treated and the desired results of the treatment.

EXAMPLES

The following examples further describe and demonstrate particular embodiments within the scope of the present Invention. The examples are given solely for illustration and are not to be construed as limitations as many variations are possible without departing from spirit and scope of the Invention.

Example I

| Ingredients | Amount (mg) |
|---|---|
| zidovudine | 300.00 |
| lamivudine | 150.00 |
| microcrystalline cellulose NF | 269.63 |
| sodium starch glycoiate NF | 22.50 |
| colloidal silicone dioxide NF | 2.25 |
| magnesium stearate | 5.63 |

Example II

Preparation

The quantities of the present example of manufacturing procedure are based on a typical batch size of 400 kg and may be adjusted depending on batch size.

First, the components are weighed from bulk containers in the following amounts:

| Ingredients | Amount (kg) |
|---|---|
| zidovudine | 160.00 |
| lamivudine | 80.00 |
| microcrystalline cellulose NF | 143.80 |
| sodium starch glycolate NF | 12.00 |
| colloidal silicone dioxide NF | 1.20 |

What is claimed is:

1. A pharmaceutical composition comprising a first active pharmaceutical ingredient and a second active pharmaceutical ingredient, and a pharmaceutically acceptable glidant ingredient, wherein:
   (i) a first active pharmaceutical ingredient is lamivudine or a pharmaceutically acceptable derivative thereof,
   (ii) a second active pharmaceutical ingredient is zidovudine or a pharmaceutically acceptable derivative thereof, and
   (iii) silicon dioxide is present as a glidant ingredient in an amount from about 0.05% to about 10% by weight based on the total weight of all ingredients.

2. The composition according to claim 1, further comprising another glidant ingredient selected from the group consisting of: powdered cellulose, microcrystalline cellulose, metallic stearates, sodium aluminosilicate, sodium benzoate, calcium carbonate, and combinations thereof.

3. The composition according to claim 2, wherein the metallic stearates are selected from the group consisting of: calcium stearate, magnesium stearate, zinc stearate, and combinations thereof.

4. The composition according to claim 2, further comprising another glidant ingredient selected from the group consisting of: calcium silicate, corn starch, magnesium carbonate, asbestos free talc, stearowet C, starch, starch 1500, magnesium lauryl sulfate, magnesium oxide, and combinations thereof.

5. A composition according to claim 1, in the form of a tablet.

6. The composition according to claim 5, wherein the lamivudine or a pharmaceutically acceptable derivative thereof is present in an amount from about 15 to about 1500 mg per tablet and the zidovudine or a pharmaceutically acceptable derivative thereof is present in an amount from about 30 to about 1000 mg per tablet.

7. The composition according to claim 6, wherein the amount of lamivudine or pharmaceutically acceptable derivative thereof is from about 100 to about 500 mg per tablet.

8. The composition according to claim 7, wherein the amount of lamivudine or pharmaceutically acceptable derivative thereof is 150 mg per tablet.

9. The composition according to claim 5, wherein the amount of zidovudine or pharmaceutically acceptable derivative thereof is from about 200 to about 500 mg per tablet.

10. The composition according to claim 9, wherein the amount of zidovudine or pharmaceutically acceptable derivative thereof is 300 mg per tablet.

11. The composition according to claim 5, wherein the lamivudine or pharmaceutically acceptable derivative thereof is substantially free of the (+)enantiomer of lamivudine or derivative thereof.

12. The composition according to claim 5, wherein the (+)enantiomer of lamivudine or pharmaceutically acceptable derivative thereof is not more than about 5% w/w of the total amount of lamivudine or derivative thereof.

13. The composition according to claim 12, wherein the (+)enantiomer of lamivudine pharmaceutically acceptable derivative thereof is not more than about 1% w/w of the total amount of lamivudine or derivative thereof.

14. The composition according to claim 5, wherein the tablet is coated with a pharmaceutically acceptable coating.

15. A method for treating, reversing, reducing or inhibiting retroviral infections by administering one or more tablets according to claim 5.

16. The method for treating, reversing, reducing or inhibiting retroviral infections according to claim 15, wherein the retrovirus is an immunodeficiency virus, including HIV.

17. An article of manufacture comprising:
 (i) packaging material; and
 (ii) one or more tablets according to claim 5 and contained within the packaging material.

18. An article of manufacture according to claim 17, additionally comprising a brochure containing product information.

19. An article of manufacture according to claim 17, wherein the packaging material is unit dose blister packaging.

* * * * *

UNITED STATES PATENT AND TRADEMARK OFFICE
CERTIFICATE OF CORRECTION

PATENT NO. : 6,113,920
DATED : September 5, 2000
INVENTOR(S) : Maye et al.

Page 1 of 1

It is certified that error appears in the above-identified patent and that said Letters Patent is hereby corrected as shown below:

Column 4,
Line 24, "that is to say than about" should read -- that is to say no more than about --

Column 7,
Example I, "sodium starch glyciate" should read -- sodium starch glycolate --

Signed and Sealed this

Twenty-seventh Day of November, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO.    : 6,113,920
DATED         : September 5, 2000
INVENTOR(S)   : Maye et al.

It is certified that error appears in the above-identified patent and that said Letters Patent is hereby corrected as shown below:

<u>Column 8,</u>
Line 10, please insert:

--Magnesium stearate              3.00

The components are then sieved using a Russell-SIV equipped with 14 mesh (1.4 mm opening) or an equivalent sieve and mesh, and deposited into a stainless-steel blending container.

The zidovudine, lamivudine, microcrystalline cellulose NF, sodium starch glycolate NF, and colloidal silicone dioxide NF are blended for 20 minutes using a suitable blender, such as a Matcon-Buls bin-type blender, a V-blender or equivalent. The magnesium stearate is then added to the mixture and blending is continued for approximately 2 minutes The lubricated blend is then compressed using a suitable rotary tablet press, typically a Courtoy R-190, R-200 or equivalent. In-process controls for tablet weight and hardness are applied at appropriate intervals throughout the compression run and adjustments to the tablet press are made as necessary.--

Signed and Sealed this

Thirtieth Day of September, 2003

JAMES E. ROGAN
*Director of the United States Patent and Trademark Office*